United States Patent [19]

Elliott, Jr.

[11] 4,287,425
[45] Sep. 1, 1981

[54] CONSTRUCTION OF A CT SCANNER USING HEAVY IONS OR PROTONS

[75] Inventor: Donald O. Elliott, Jr., Baltimore, Md.

[73] Assignee: Pfizer, Incorporated, New York, N.Y.

[21] Appl. No.: 108,831

[22] Filed: Dec. 31, 1979

[51] Int. Cl.[3] .............................................. G01K 1/08
[52] U.S. Cl. ................................ 250/445 T; 250/398; 313/57; 313/62
[58] Field of Search .............. 250/398, 445 T; 313/55, 313/57, 60, 62

[56] References Cited

U.S. PATENT DOCUMENTS

| | | | |
|---|---|---|---|
| 4,045,672 | 8/1977 | Watanabe | 250/445 T |
| 4,122,346 | 10/1978 | Enge | 250/398 |
| 4,130,759 | 12/1978 | Haimson | 250/445 T |

Primary Examiner—Davis L. Willis
Attorney, Agent, or Firm—Larry S. Nixon

[57] ABSTRACT

A computed tomography X-ray scanner, in which a monochromatic X-ray beam is generated by irradiating an X-ray producing target with high energy monoenergetic ions. The ion beam is preferably produced by a cyclotron. The X-ray beam is preferably rotated through an object to be scanned by angularly displacing the ion beam and target about the center axis of the object. A conventional X-ray detector array, a signal and data processor and imaging means are provided to convert detected X-ray absorption measurements into a two-dimensional visual image of the scanned object cross-section.

20 Claims, 3 Drawing Figures

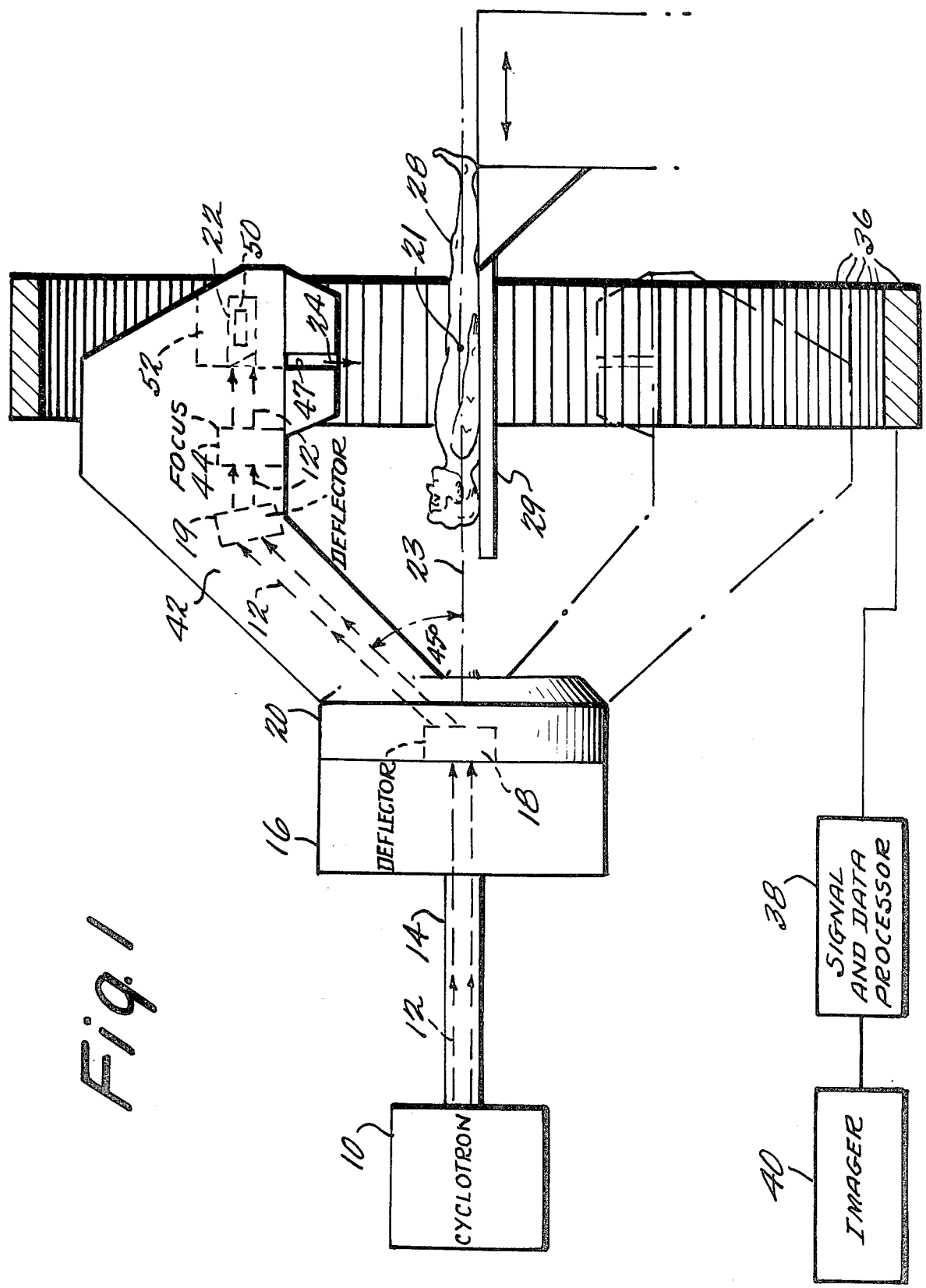

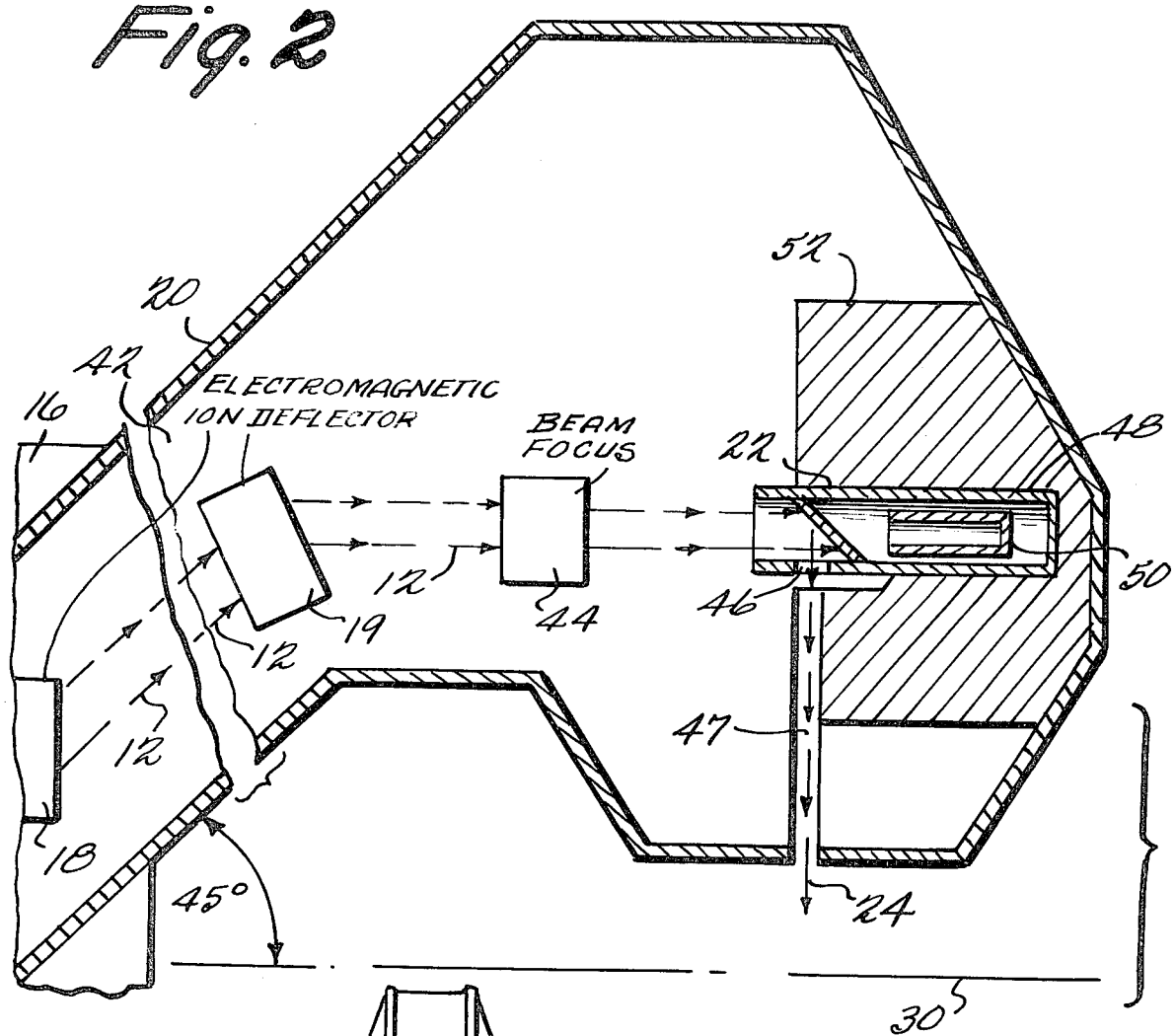

CONSTRUCTION OF A CT SCANNER USING HEAVY IONS OR PROTONS

BACKGROUND OF THE INVENTION

The invention relates generally to radiant energy imaging, and more particularly to a novel apparatus and technique for producing and directing high intensity X-rays to an object of interest from a plurality of preselected points spaced from that object so as to obtain a cross-sectional image thereof. More specifically, the invention relates to a computed tomography (CT) X-ray scanner in which the X rays are produced using a source of high energy ions impinging on a target material.

The field of CT scanners has seen substantial improvements in recent years and has now advanced to a so called "fourth generation". Such a "fourth generation" device is disclosed in the copending patent application Ser. No. 726,556 of Stein, filed Sept. 22, 1976. That CT scanner includes an X-ray source (such as an X-ray tube containing a tungsten filament), which generates a fan beam and which is rotated in a circular arc about an axis along which a patient or other object to be examined is disposed. A stationary array of contiguous X-ray detectors is arranged in a circle outside the circumferential path of the X-ray source for converting incident X-rays into corresponding detected electrical signals. The outputs from the X-ray detectors are logarithmically amplified, digitized and input to a computer for generating an array of pixel image values which are then displayed in two dimensions on a CRT screen as corresponding luminance values, representing a cross section of the patient or object.

A CT scanner which includes no moving parts is disclosed in U.S. Pat. No. 4,130,759 issued to Haimson. This device includes a fixed annular target from which an X-ray beam is selectively directed toward the patient. The X-ray beam is generated by a high power electron beam in a bell-shaped evacuated housing. The electron beam may be selectively electronically directed to any point on the target.

In each of the above-described CT scanners, the X-rays are typically generated by a beam of electrons impinging on a target material such as tungsten. The electrons in the electron beam travel at a range of speeds and cause a broad Bremstralung spectrum of X-rays to be emitted by the target when the electrons are decelerated by collisions with individual atoms in the target. The wide spectrum of X-rays generated results in the well known "beam hardening" or "spectral hardening" problem. This problem results because the degree of X-ray absorption by the body is a function of the energy spectrum of the X-rays (low energy X-rays are preferentially absorbed), which function varies according to the particular body matter lying along the X-ray beam path.

As a result, the measured logarithmic attenuation of the X-ray beam is not a strictly linear function of the body thickness. Rather, the intensity of the X-ray beam received by an X-ray detector is a very complex function of the X-ray energy spectrum and the quality and quantity of matter between the X-ray source and the X-ray detector. In order to eliminate or compensate for beam hardening, shields may be utilized to reduce the reception by the body of low energy photons and complex computer programs have been devised to compensate for the beam hardening which remains. However, these techniques have never been completely successful, primarily because of the nonlinear functional relationship between the output X-ray beam spectrum and the input X-ray spectrum for different materials in the X-ray path.

BRIEF SUMMARY OF THE INVENTION

In accordance with the present invention the above described problems with prior CT scanners are overcome. In accordance with the present invention, high energy, monoenergetic protons or ions are directed at a suitable target material in order to obtain a substantially monochromatic X-ray beam which is in turn directed in a scanning pattern, as in prior CT scanners. An exemplary embodiment of the CT scanner of the present invention includes a stationary detector, a source of high energy monoenergetic ions, and a target at which the ions are directed to produce a beam of monochromatic X-rays. By rotating the ion beam alone, or by rotating both the beam and the target, the X-ray beam is caused to rotationally scan the patient.

It is well known (a) that a charged particle beam interacts with target atoms in its path to create inner-shell vacancies, (b) that one of the causes of such ionization is atomic Coulomb excitation (primary ionization), and (c) that primary ionization can be followed by the emission of specific X rays characteristic of the target atoms. This process is discussed with respect to heavy atoms such as tungsten in a paper authored by G. Deconninck and M. Longree, "K-shell Ionization of Heavy Atoms by 40–110 MeV Particles", Physical Review A, Vol. 16, No. 4, (October, 1977). Although at lower energies (e.g. 100–300 keV), the ionization potential for X-ray target material such as tungsten is much greater for electrons than for ions, a rate of K-shell ionization sufficient to obtain a flux of X-rays for CT scanner purposes can be obtained only at much higher energies, e.g. 25–160 MeV, where the ionization cross section of X-ray target material is much greater for high energy ions than for electrons. Thus, a much higher flux of K-shell X-rays can be obtained using protons or ions such as $He^{++}$.

These principles have heretofore been applied only in research applications as for example in the study of inner shell ionization of heavy atoms. See e.g. Woods, C. W., et al "Anomalous Target Z Dependence of Double to Single K-Shell Vacancy Production in Cl-Beam X Rays," Physical Review Letters, Volume 31, Number 1, (July 2, 1973); Hopkins, F., et al, "Multiple Inner-Shell Ionization of Aluminum by High-Velocity Medium-Z Beams," Physical Review Letters, Volume 8, Number 6, (December, 1973); and Kauffman, R. L., et al "X-ray Decay Energies of Highly Ionized Florine Atoms," J. Phys. B: Atom. Molec. Phys., Volume 6, (October, 1973).

The present invention applies these principles to CT Scanners. Thus, the basic elements of the present invention may be summarized as follows:

1. a target comprised of atoms such as tungsten which are ionizable by high energy ions so as to emit X-rays having energies in a very narrow energy interval;

2. an X-ray detector spaced opposite from the target; and 3. structure for producing an X-ray beam extending from the target through the object to be studied, the beam in the examplary embodiment being rotatable in an arc about an axis extending through the object, the structure including a source of high energy, monoenergetic ions focusable on the target so as to produce the X-ray beam.

In accordance with one embodiment of the invention, the ion beam is guided by a rotatable waveguide from a cyclotron at one end of the waveguide to a target fixed at the other end of the waveguide so that the X-ray beam may be rotated by rotating the waveguide and target. As in other "fourth generation" CT scanners, the object to be studied is placed on the target's axis of rotation. In another embodiment of the invention, the ion beam originates in a cyclotron and is deflected within an evacuated bell-shaped housing toward preselected points on a fixed annular target. X-rays are then emitted from target toward the object to be studied which lies along the annular target's center axis.

BRIEF DESCRIPTION OF THE DRAWING

These and other aspects and advantages of the invention will be better understood from the following detailed description of the preferred embodiments of the invention with reference to the appended drawings in which:

FIG. 1 is a schematic illustration of the presently preferred exemplary embodiment of the present invention;

FIG. 2 is a partially schematic vertical cross section of rotatable head portion of the invention shown in FIG. 1; and FIG. 3 is an end elevation of the head portion of the embodiment shown in FIGS. 1 and 2.

DETAILED DESCRIPTION OF THE PREFERRED EMBODIMENT

Referring to FIG. 1 and to FIG. 2, there is shown an exemplary embodiment of a CT scanner system in accordance with the present invention. The CT scanner system includes a cyclotron 10 for generating an ion beam 12 which is directed through evacuated beam pipes 14 to a rigid entry structure 16. Entry structure 16 supports a head structure 20 which receives the ion beam 12 and which can be rotated about an isocenter 21 on rotational axis 30. Head structure 20 contains two electromagnetic ion deflectors 18 and 19 which deflect the ion beam within the head structure to a tungsten target 22. The interaction of beam 12 with target 22 causes a substantially monochromatic beam of K-$\beta$ and K-$\alpha$ X-rays 24 to be directed from head structure 20 through the object to be studied, e.g., the patient 28, which is reclining on a table 29 along a horizontal axis which coincides with rotational axis 30. As is illustrated in FIG. 3, the X-ray beam 24 is suitably a fan beam of X-rays which subtends an angle sufficiently wide to illuminate the patient circle 34 centered on axis 30.

Referring back to FIGS. 1 and 2, the X-ray beam 24 which passes through the patient 28 is received by an array of detectors 36 which extend contiguously in a circle about axis 30, outside the circular path of the head structure 20. At a given moment, X-ray beam 24 simultaneously illuminates a contiguous group of individual detectors 36 to provide a corresponding number of detected signals, each representative of the X-ray transmissivity between target 22 and a respective one of detectors 36. A signal and data processor 38 is connected to detectors 36 for conventionally processing the detector output signals and to drive an imager 40 (e.g., a CRT), thus providing an image representative of the X-ray absorption/transmissivity of a cross-sectional plane within the patient circle 34 which has been scanned. The scanning system and patient may be relatively displaced axially to produce a sequence of images of corresponding axially displaced cross-sections. The detectors 36, signal and data processor 38 and imaging means 40 may be of conventional design, as for example as described in the copending Stein application, Ser. No. 726,556, referred to above.

Examining rotatable head structure 20 in detail, it includes an evacuated channel 42 which extends from deflection magnet 18, at a 45 degree angle to axis 30, to deflection magnet 19. Deflection magnet 18 deflects ion beam 12 through channel 42 to deflection magnet 20. Deflection magnet 19 deflects the ion beam 12 in a horizontal direction (parallel to axis 30) through a focusing device 44. Focusing device 44 focuses the beam of ions 12 toward tungsten target 22. Target 22 comprises a thin plate of tungsten disposed at a 45 degree angle to the impinging ion beam 12. A plate thickness of several millimeters is suitable although a plate thickness of 0.5 mm. is acceptable. Directly below target 22 is a beryllium window 46 which separates the target 22 from an open passage 47 which collimates the X-ray beam 24 radially inward toward axis 30. Behind target 22 is a stainless steel vacuum chamber 48 in which is disposed a water cooled copper Faraday cup 50 for measuring the number of ions passing through the target 22. A beam dump, consisting of lead shielding 52, completely surrounds the outside surface of a rear surface of the stainless steel vacuum chamber 48 and target 22 in order to absorb the beam of ions which pass through target 22.

Since the target is relatively thin, most of the ions in ion beam 12 will pass through the target 22. As a result heat energy absorbed by the target will be minimal and special cooling, as is required in convention electron beam CT scanners, will generally not be necessary. Conventional water cooling can, however, be provided adjacent to the target in particular embodiments of the invention where deemed necessary. Since target overheating can be a significant problem in prior conventional CT scanners, the ion beam X-ray generation of the present invention provides a significant advantage in this regard.

It is desirable that the ionization cross section of the target be maximized so as to maximize the X-ray production efficiency of the device. For example, for protons impinging upon a tungsten target, the peak ionization cross section is obtained when the protons have a kinetic energy of 147 MeV. However, protons above 25 MeV can be used to produce an adequate X-ray beam intensity. The 42 MeV cyclotron manufactured by the Cyclotron Corporation, model CP-42, which develops a proton beam current of 78 $\mu$A, and Cyclotron Corporation's model CP-30, 30 MeV cyclotron which develops a proton beam current of 100 $\mu$A, each provide a beam of protons with adequate energy for CT scanner X-ray beam production purposes while being sufficiently compact as to be feasibly disposed in a hospital building.

Although only a preferred embodiment of the invention is disclosed in detail above, for illustrative purposes, it will be understood that variations and modifications of the disclosure which lie within the scope of the appended claims are fully contemplated. For example, in one alternate embodiment of the invention, an annular tungsten target adapted to surround the patient is provided together with means for angularly deflecting a monoenergetic beam of ions against the target. An X-ray beam is thereby rotated from the annular target toward a patient who lies along the center axis of the annulus. Similar deflection structure for deflecting electrons against an annular tungsten target are disclosed in U.S. Pat. No. 4,045,672 issued to Watanabe and U.S. Pat. No. 4,130,759, issued to Haimson.

What is claimed is:

1. An apparatus for obtaining a two dimensional display of the X-ray absorption distribution within a cross sectional volume of an object disposed along an axis, comprising
   a target;
   an X-ray detector spaced opposite said target; and
   means for producing a substantially monochromatic X-ray beam extending from said target through said axis to said detector including means for angularly displacing said beam about said axis so as to scan said object in said cross-sectional volume;
   said X-ray detector including means for converting said X-ray beam into a corresponding detected electrical signal;
   said X-ray beam producing means including a source of high energy substantially monoenergetic ions focusable on said target; and
   said target including atoms which are ionized by said high energy ions so as to emit substantially monochromatic X-rays.

2. Apparatus in claim 1 wherein said source of substantially monoenergetic high energy ions comprises a cyclotron.

3. Apparatus as in claim 1 wherein said high energy ions comprise $H^{30}$ ions.

4. Apparatus as in claim 1 wherein said high energy ions comprise $He^{++}$ ions.

5. Apparatus as in claim 2 wherein said target comprises a thin wall of tungsten.

6. Apparatus as in claim 5 wherein said thin wall of tungsten has a thickness which exceeds 0.5 mm.

7. Apparatus as in claim 1 wherein said X-ray beam displacing means comprises means for angularly displacing said target about said axis.

8. Apparatus as in claim 7 wherein said detecting means comprises an array of contiguous X-ray energy detector elements arranged about said axis; each of said elements being responsive to incident X-rays for converting said incident X-rays into corresponding detected signals.

9. Apparatus as in claim 1 wherein said source of high energy substantially monoenergetic ions comprises a source of ions having kinetic energies in excess of 2 MeV.

10. Apparatus as in claim 1 wherein said source of high energy substantially monoenergetic ions comprises a source of ions having kinetic energies in excess of 25 MeV.

11. An apparatus as in claim 8 wherein said array of detector elements substantially encircles said axis.

12. A method for obtaining a two dimensional display of the X-ray absorption distribution in a cross-sectional volume of an object disposed along an axis, said method comprising the steps of:
   (1) producing a beam of substantially monoenergetic high energy ions;
   (2) directing said beam of ions at a target, said target emitting substantially monochromatic X-rays in response to said substantially monoenergetic ions incident thereon;
   (3) directing a beam of said substantially monochromatic X-rays toward said axis and through said object from a plurality of points spaced equidistant from said axis; and
   (4) detecting said X rays after passage through said object to produce a sequence of detected electrical signals representative of X-ray absorption within said object.

13. Method as in claim 12 wherein said step of producing a beam of substantially monoenergetic ions comprises the step of generating said beam of ions in a cyclotron.

14. Method as in claim 12 wherein said step of directing a beam of substantially monochromatic X-rays comprises the step of moving said target in a circular path about said axis.

15. An improved computed tomography X-ray scanner of the type having an X-ray producing target, an X-ray detector spaced opposite said target and arranged to receive an X-ray beam emerging from said target, said detector including means for converting said X-ray beam into a coresponding detected electrical signal, said improvement comprising
   a source of substantially monoenergetic high energy ions arranged to impinge upon said target and to thereby cause said X-ray beam to be substantially monochromatic.

16. An improved computed tomography X-ray scanner as in claim 15 wherein said source of substantially monoenergetic high energy ions comprises a cyclotron.

17. Apparatus as in claim 15 wherein said high energy ion comprise $H^+$ ions.

18. Apparatus as in claim 15 wherein said high energy ions comprise $He^{++}$ ions.

19. Apparatus as in claim 16 wherein said target comprises a thin wall of tungsten having a thickness in excess of 0.5 mm.

20. Apparatus as in claim 15 wherein said source of high energy substantially monoenergetic ions comprises a source of ions having kinetic energies in excess of 25 MeV.

* * * * *